(12) United States Patent
Saroka et al.

(10) Patent No.: US 11,712,169 B2
(45) Date of Patent: *Aug. 1, 2023

(54) ELECTROMAGNETIC (EM) PROBES, METHODS OF USING SUCH EM PROBES AND SYSTEMS WHICH USE SUCH ELECTROMAGNETIC EM PROBES

(71) Applicant: Sensible Medical Innovations Ltd., Netanya (IL)

(72) Inventors: Amir Saroka, Herzlia (IL); Leonid Voshin, Kfar-Saba (IL); Yiftach Barash, Tel-Aviv (IL); Benyamin Almog, Kibbutz Givat Brenner (IL); Tal Levi, Tel-Aviv (IL)

(73) Assignee: Sensible Medical Innovations Ltd., Netanya (IL)

( * ) Notice: Subject to any disclaimer, the term of this patent is extended or adjusted under 35 U.S.C. 154(b) by 81 days.

This patent is subject to a terminal disclaimer.

(21) Appl. No.: 17/156,718

(22) Filed: Jan. 25, 2021

(65) Prior Publication Data
US 2021/0137404 A1    May 13, 2021

Related U.S. Application Data

(63) Continuation of application No. 16/355,946, filed on Mar. 18, 2019, now Pat. No. 10,898,102, which is a
(Continued)

(51) Int. Cl.
*A61B 5/05* (2021.01)
*A61B 5/0507* (2021.01)
(Continued)

(52) U.S. Cl.
CPC .............. *A61B 5/05* (2013.01); *A61B 5/0507* (2013.01); *H01Q 9/27* (2013.01); *H01Q 1/36* (2013.01);
(Continued)

(58) Field of Classification Search
CPC ..... A61B 5/05; A61B 5/0507; A61B 2562/02; G01R 29/08; G01R 29/0814;
(Continued)

(56) References Cited

U.S. PATENT DOCUMENTS

| 5,724,052 A | 3/1998 | Boulingre et al. |
| 2003/0036674 A1 | 2/2003 | Bouton |

(Continued)

FOREIGN PATENT DOCUMENTS

| DE | 10304420 | 10/2004 |
| JP | 2011-250031 | 12/2011 |
| WO | WO 2013/105086 | 7/2013 |

OTHER PUBLICATIONS

Applicant-Initiated Interview Summary dated Mar. 19, 2018From the US Patent and Trademark Office Re. U.S. Appl. No. 14/370,777. (4 pages).
(Continued)

*Primary Examiner* — Carolyn A Pehlke

(57) ABSTRACT

An electromagnetic (EM) probe for monitoring at least one biological tissue. The EM probe comprises a spiral antenna conductor (not shown) and an EM radiation absorbing layer (92) mounted along the antenna. The EM radiation absorbing layer has a plurality of substantially concentric frame shaped regions (93A-C) corresponding to portions of said spiral antenna having equal surface of antenna conductor,
(Continued)

any of said plurality of concentric frame shaped regions has an EM radiation absorption coefficient different than any other of said neighboring concentric frame shaped regions.

18 Claims, 10 Drawing Sheets

Related U.S. Application Data continuation of application No. 14/370,777, filed as application No. PCT/IL2013/050010 on Jan. 3, 2013, now Pat. No. 10,231,641.

(60) Provisional application No. 61/583,210, filed on Jan. 5, 2012.

(51) Int. Cl.
    *H01Q 9/27*     (2006.01)
    *H01Q 1/36*     (2006.01)
    *H01Q 17/00*    (2006.01)

(52) U.S. Cl.
    CPC ........ *H01Q 17/00* (2013.01); *Y10T 29/49016* (2015.01)

(58) Field of Classification Search
    CPC .. G01R 29/0878; H01Q 17/00; H01Q 17/001; H01Q 17/002; H01Q 17/004; H01Q 17/005; H01Q 17/007; H01Q 17/008; H01Q 1/36; H01Q 1/38; H01Q 11/105; H01Q 13/18; H01Q 15/14; H01Q 1/273; H01Q 1/40; H01Q 21/06; H01Q 21/065; H01Q 21/20; H01Q 9/0407; H01Q 9/0414; H01Q 9/27; G01N 22/00
    See application file for complete search history.

(56) References Cited

U.S. PATENT DOCUMENTS

| | | |
|---|---|---|
| 2007/0018899 A1 | 1/2007 | Kunysz et al. |
| 2009/0062637 A1 | 3/2009 | Hashimshony et al. |
| 2010/0134371 A1 | 6/2010 | Worl |
| 2011/0178574 A1 | 7/2011 | Hardy et al. |
| 2011/0234471 A1 | 9/2011 | Tanabe et al. |
| 2014/0378813 A1 | 12/2014 | Saroka et al. |
| 2019/0209039 A1 | 7/2019 | Saroka et al. |

OTHER PUBLICATIONS

Communication Pursuant to Article 94(3) EPC dated Mar. 30, 2016 From the European Patent Office Re. Application No. 13705260.1.
Communication Pursuant to Article 94(3) EPC dated Jan. 31, 2017 From the European Patent Office Re. Application No. 13705260.1. (3 Pages).
Communication Pursuant to Article 94(3) EPC dated Jul. 31, 2015 From the European Patent Office Re. Application No. 13705260.1.
International Preliminary Report on Patentability dated Jul. 17, 2014 From the International Bureau of WIPO Re. Application No. PCT/IL2013/050010.
International Search Report and the Written Opinion dated Apr. 24, 2013 From the International Searching Authority Re. Application No. PCT/IL2013/050010.
Notification of Office Action and Search Report dated Mar. 7, 2016 From the State Intellectual Property Office of the People's Republic of China Re. Application No. 201380012620.0 and its Summary in English.
Office Action dated Apr. 11, 2019 From the Israeli Patent Office Re. Application No. 233511 and its Translation Into English. (5 Pages).
Office Action dated Feb. 11, 2018 From the Israeli Patent Office Re. Application No. 233511 and its Translation Into English. (6 Pages).
Office Action dated Sep. 24, 2020 From the Israel Patent Office Re. Application No. 271450. (3 Pages).
Official Action dated Jun. 7, 2018 From the US Patent and Trademark Office Re. U.S. Appl. No. 14/370,777. (9 pages).
Official Action dated Jan. 12, 2017 From the US Patent and Trademark Office Re. U.S. Appl. No. 14/370,777. (14 pages).
Official Action dated Nov. 14, 2017 From the US Patent and Trademark Office Re. U.S. Appl. No. 14/370,777. (10 pages).
Official Action dated Jun. 15, 2016 From the US Patent and Trademark Office Re. U.S. Appl. No. 14/370,777.
Summons to Attend Oral Proceedings Pursuant to Rule 115(1) EPC dated Oct. 30, 2017 From the European Patent Office Re. Application No. 13705260.1. (6 Pages).
Translation Dated Jan. 6, 2021 of Office Action dated Sep. 24, 2020 From the Israel Patent Office Re. Application No. 271450. (2 Pages).
Kong et al. "Magnetic and Microwave Absorbing Properties of Magnetite-Thermoplastic Natural Rubber Nanocomposites", Journal of Magnetism and Magnetic Materials 322(21): 3401-3409, Nov. 30, 2010.
Strong "Theoretical Basis of the Bouguer-Beer Law of Radiation Absorption", Analytical Chemistry, 24(2): 338-342, Feb. 1952.
Wikipedia "Absorption (Electromagnetic Radiation)", Wikipedia, the Free Encyclopedia, 3 P., Last Modified Mar. 17, 2016.

ELECTROMAGNETIC (EM) PROBES, METHODS OF USING SUCH EM PROBES AND SYSTEMS WHICH USE SUCH ELECTROMAGNETIC EM PROBES

RELATED APPLICATIONS

This application is a continuation of U.S. patent application Ser. No. 16/355,946 filed on Mar. 18, 2019, which is a continuation of U.S. patent application Ser. No. 14/370,777 filed on Jul. 6, 2014, now U.S. Pat. No. 10,231,641, which is a National Phase of PCT Patent Application No. PCT/IL2013/050010 having International Filing Date of Jan. 3, 2013, which claims the benefit of priority under 35 USC § 119(e) of U.S. Provisional Patent Application No. 61/583,210 filed on Jan. 5, 2012. The contents of the above applications are all incorporated by reference as if fully set forth herein in their entity.

FIELD AND BACKGROUND OF THE INVENTION

The present invention, in some embodiments thereof, relates to an electromagnetic EM probe and, more particularly, but not exclusively, to an EM probe for transmission and/or reception of electromagnetic radiation and a method of generating the EM probe.

EM radiation, such as RF and MW radiation, is a useful means of monitoring and diagnosing body tissues. The dielectric properties of the tissues may be a basis of detecting various pathologies and physiological trends.

Examples for using RF and MW radiation for monitoring and diagnosing body tissues are found, inter alia, in International patent application pub. No WO 2010/100649, International patent application pub. No WO 2009/031150, and/or International patent application pub. No 2009/031149, which are incorporated herein by reference.

During the last years, various EM probes have been developed. For example U.S. Pat. No. 7,184,824 describes an EM probe for examining tissue in order to differentiate it from other tissue according to the dielectric properties of the examined tissue. The EM probe includes an inner conductor, having a plurality of sharp, thin, conductive spikes, at a proximal end with respect to a tissue for examination, the plurality of sharp, thin, conductive spikes being operative to enhance the electrical fringe fields, where interaction with the tissue for examination occurs.

Another example is described in U.S. Pat. No. 7,591,792 which describes: a tissue sensors house for one or more sensor elements. Each element has a housing mounted substrate and a superstrate with a planar antenna between. A transitional periphery (TP) of a superstrate outer surface interconnects a base to a plateau. At least some of the TP has a generally smooth transition. Plural elements are spaced by the housing. Alternately, the superstrate TP is flat, the housing extends to the outer superstrate surface and a shield surrounds the element. The housing is flush with or recessed below the superstrate and defines a TP between the housing and superstrate. A method converts a reference signal to complex form; plots it in a complex plane as a reference point (RP); converts a measurement signal to complex form; plots it in the complex plane as a measurement point (MP); determine a complex distance between the MP and the RP; and compares complex distance to a threshold.

SUMMARY OF THE INVENTION

According to some embodiments of the present invention, there is provided an electromagnetic (EM) probe for monitoring at least one biological tissue. The EM probe comprises a spiral antenna and an EM radiation absorbing layer mounted along the antenna. The EM radiation absorbing layer has a plurality of substantially concentric frame shaped regions corresponding to portions of the spiral antenna having equal surface of antenna conductor, any of the plurality of concentric frame shaped regions has an EM radiation absorption coefficient greater than any other of the concentric frame shaped regions it encloses.

Optionally, the spiral antenna is a wideband antenna.

Optionally, the antenna is multi-frequency antenna.

Optionally, the EM radiation absorption coefficient of a given frame shape region is a function of the integral sum of the amount of EM radiation absorbing layer along the effective perimeters associated with the frame shape region.

Optionally, EM radiation absorbing layer is mounted in a common plane with a conductive element of the antenna.

Optionally, EM radiation absorbing layer is positioned to suppress EM currents.

Optionally, the plurality of substantially concentric frame shaped regions comprises at least three substantially concentric frame shaped regions.

Optionally, the EM probe is part of an EM probe having a plurality of similar EM probes.

Optionally, a plurality of the substantially concentric frame shaped regions are selected to match the contour of the spiral antenna.

Optionally, the plurality of substantially concentric frame shaped regions frames a shape having essentially no EM radiation absorbing layer.

Optionally, at least one of density and concentration of a radiation absorbing material in the a plurality of substantially concentric frame shaped regions decreases from an outer periphery of the EM radiation absorbing layer to a central point of the EM radiation absorbing layer.

More optionally, the EM probe of claim 11, wherein the central point coincides with the boresight of the antenna.

More optionally, the EM probe of claim 11, wherein the central point coincides with a feeding point of the antenna.

More optionally, the central point coincides with a geometric center of the antenna.

Optionally, the thickness of a radiation absorbing material in the a plurality of substantially concentric frame shaped regions decreases from an outer periphery of the EM radiation absorbing layer towards a central point of the EM radiation absorbing layer.

Optionally, a ratio between an EM radiation absorbing material having a first EM radiation absorbing coefficient and another material having a second EM radiation absorbing coefficient in the a plurality of substantially concentric frame shaped regions decreases from an outer periphery of the EM radiation absorbing layer towards a central point of the EM radiation absorbing layer.

Optionally, at least some of the plurality of substantially concentric frame shaped regions comprises a first concentric frame shaped region segment made of a radiation absorbing material and a second concentric frame shaped region segment made of a member of a group consisting of: an additional radiation absorbing material having a lower radiation absorption coefficient than the radiation absorbing material and an additional radiation absorbing material having no radiation absorbing material.

Optionally, the EM radiation absorbing layer having ratio between a real magnetic permeability and an imaginary magnetic permeability of at least 0.01 for at least some the frequencies within a range between 100 Megahertz (MHz) and 5 gigahertz (GHz).

More optionally, the ratio is at least 0.1.

Optionally, the EM radiation absorbing layer having a ratio between an imaginary electric permeability and a real electric permeability of at least 0.01 for at least some the frequencies within a range between 100 Megahertz (MHz) and 5 Gigahertz (GHz).

Optionally, the antenna is a horn or conic antenna. The EM radiation absorbing layer coats inner surfaces of the antenna, and the radiation absorption coefficient increases as a function of a distance from a feeding point of the antenna.

Optionally, the EM radiation absorbing layer encloses a feed of the EM antenna.

More optionally, the EM radiation absorbing layer has at least one jagged edge having a tip pointing toward the feed.

Optionally, the EM absorbing layer comprises an EM absorbing layer being essentially parallel to a surface of the EM antenna.

More optionally, the EM radiation absorbing layer has a star shaped cutout set so that a geometric center thereof coincides with a boresight of the spiral antenna.

Optionally, the EM radiation absorbing layer comprises a plurality of different absorbing materials having a plurality of different EM radiation absorption coefficients distributed in the plurality of substantially concentric frame shaped regions.

Optionally, the EM radiation absorbing layer is configured such that the innermost concentric frame shaped regions that are associated with the innermost 10% or more of the surface of the antenna conductor absorb only 5% or less of the total amount of EM radiation absorbed by the EM radiation absorbing layer.

Optionally, the EM radiation absorbing layer is configured such that the innermost concentric frame shaped regions that are associated with the innermost 25% or more of the surface of the antenna conductor absorb only 10% or less of the total amount of EM radiation absorbed by the EM radiation absorbing layer.

Optionally, the EM radiation absorbing layer is configured such that the innermost concentric frame shaped regions that are associated with the innermost 50% or more of the surface of the antenna conductor absorb only 25% or less of the total amount of EM radiation absorbed by the EM radiation absorbing layer.

Optionally, the EM radiation absorbing layer is configured such that the innermost concentric frame shaped regions that are associated with the innermost 50% or more of the surface of the antenna conductor absorb only 10% or less of the total amount of EM radiation absorbed by the EM radiation absorbing layer.

Optionally, the EM radiation absorbing layer is configured such that the innermost concentric frame shaped regions that are associated with the innermost 50% or more of the surface of the antenna conductor absorb only 5% or less of the total amount of EM radiation absorbed by the EM radiation absorbing layer.

More optionally, the EM radiation absorption is measured with respect to the frequencies of EM radiation that are radiated most efficiently from the outermost concentric frame shaped regions of the antenna spanning the outermost 64% or less of the surface area of the antenna conductor that is associated with the concentric frame shaped regions.

More optionally, the EM radiation absorption is measured with respect to the frequencies of EM radiation that are radiated most efficiently from the outermost concentric frame shaped regions of the antenna spanning the outermost 36% or less of the surface area of the antenna conductor that is associated with the concentric frame shaped regions.

An antenna array having a plurality of EM probes, each defined as described in claim 1.

Optionally, the EM radiation absorbing layers of at least two of the plurality of EM probes are part of a single continuous layer.

Optionally, the EM probe further comprises a cup shaped cavity having an opening and an interior volume, a circumferential flange formed substantially around the cup shaped cavity, in proximity to the opening, and at least one layer of a material, for absorbing electromagnetic radiation, applied over at least one of a portion of the circumferential flange and a portion of the outer surface of the cup shaped cavity.

Optionally, the EM radiation absorbing layer is included in a continuous layer.

Optionally, the EM radiation absorbing layer is multilayered.

Optionally, the EM radiation absorbing layer is sectioned to a plurality of segments.

According to some embodiments of the present invention, there is provided a method of producing an electromagnetic (EM) EM probe for monitoring at least one biological tissue. The method comprises providing a spiral antenna and applying at least one layer of an EM absorbing material over the antenna such that once applied, the layer has a plurality of substantially concentric frame shaped regions corresponding to portions of the spiral antenna having equal surface area of the conductive arms, each of the plurality of concentric frame shaped regions having EM radiation absorption coefficient greater than any other of the concentric frame shaped regions it encloses.

According to some embodiments of the present invention, there is provided a method of monitoring at least one biological tissue. The method comprises providing electromagnetic (EM) probe which comprises a spiral antenna which performs at least one of emitting and capturing EM radiation, the antenna having an EM radiation absorbing layer mounted along the antenna, wherein the EM radiation absorbing layer has a plurality of substantially concentric frame shaped regions corresponding to portions of the spiral antenna having equal surface area of the conductive arms, each of the plurality of frame shaped regions has an EM radiation absorption coefficient greater than any other concentric frame shaped region it encloses and attaching the probe to a monitored user.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 7A presents a circular spiral antenna and FIG. 7B shows an oval (elliptical) spiral antenna.

DESCRIPTION OF EMBODIMENTS OF THE INVENTION

Figure 1B:
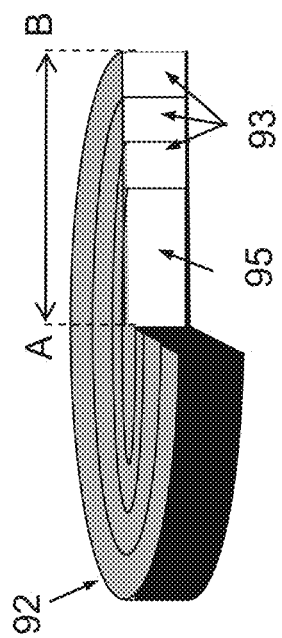
FIG. 1B is a schematic perspective representation of concentric frame shaped regions for an antenna such as the antenna of FIG. 1A, and depicting a cross section through the concentric frame shaped regions, according to some embodiments of the present invention.

The present invention, in some embodiments thereof, relates to an electromagnetic EM probe and, more particularly, but not exclusively, to an EM probe for transmission and/or reception of electromagnetic radiation and a method of generating the EM probe.

According to some embodiments of the present invention there are provided EM probes, optionally for monitoring biological tissue(s), which include a spiral antenna and an EM radiation absorbing layer mounted along the antenna and having an EM radiation absorption coefficient which increases as a function of distance from a geometric center and/or a feeding point of the antenna and/or the boresight of the antenna. Such EM radiation absorption coefficient may in some embodiments be deemed to increase from a geometric center and/or a feeding point of the antenna and/or the boresight of the antenna, even if it remains constant for a portion of the distance.

As used herein, the term spiral antenna may be taken to mean an antenna or a portion of an antenna that is configured to transmit and/or intercept a plurality of frequencies within a broad range of frequencies wherein the highest and lowest frequencies that can be transmitted by the antenna define between them the broad range. In some embodiments, the antenna is configured to transmit and/or intercept the entire broad range. In other embodiments antenna is a multi-frequency antenna, in the sense that it is configured to transmit and/or intercept two or more subsets of frequencies within the broad range, wherein the highest and lowest frequencies that can be transmitted by the antenna define between them the broad range. In some embodiments, the broad range spans a range of ±40% or more around a central frequency, or even a full octave of frequencies or more. In some embodiments, the broad range spans a 600 MHz to 4 GHz band.

This radiating element can in some embodiments be used for a single frequency, narrow band signals, multi-band signal or wideband signals utilizing low frequencies. In this aspect multi-frequency might refer to also single or multi-band signals.

As used herein, the "boresight" of an antenna is the axis of the antenna lobe having maximum gain when measured in free space.

The spiral antenna may be of any shape having one, two or more spiral arms and having a shape selected from round, oval, square and/or rectangular. The spiral antenna may or may not be planar.

The EM radiation absorbing layer may be mounted along the antenna from any direction as long as it is positioned to affect the emission of EM energy by the antenna. Optionally, the EM radiation absorbing layer is positioned in such proximity to the antenna's conductor(s) that it will attenuate EM energy by suppressing its currents. Optionally, this includes positioning the EM radiation absorbing layer at least partially in the near-field of the antenna. Optionally this includes the volume around at least a part of the conducting arm(s), with distance of the most 5, 3 or 1 times the largest distance between two adjacent conducting arms at the same location. Accordingly, the EM radiation absorbing layer may be positioned along a surface of the antenna (e.g. front and/or back) and/or the antenna may be partly or fully embedded in the EM radiation absorbing layer and/or the EM radiation absorbing layer may comprise EM radiation absorbing material positioned between the antenna arms. As used herein, EM energy may refer to EM-fields and/or currents.

The construction of EM probes as outlined above and described below may in some embodiments provide an increase of effective and usable bandwidth of EM probes having antennas in a given size. Specifically it may enable utilization of lower frequencies and/or improved smoothness of the lower band while it may at the same time also maintain high efficiency of the higher band and a smooth transition from the lower band to the higher band. Such an EM probe has a smooth spectrum behavior of both phase and amplitude antenna response. The EM probe may also improve circular polarization of the antenna specifically in the lower band.

Optionally, the EM radiation absorbing layer includes a plurality of substantially concentric frame shaped regions corresponding to portions of the antenna and having surface areas on the plane of the antenna conductors. Optionally the EM radiation absorbing layer includes a plurality of substantially concentric frame shaped regions corresponding to portions of the antenna and having equal surface of the conductive arms. Optionally the EM radiation absorbing layer includes a plurality of substantially concentric frame shaped regions corresponding to portions of the antenna and having equal loss of energy without the EM radiation absorbing layer. In this context, "equal loss" means a loss of EM energy that is not due to the EM energy being radiated. This loss may include, for example, conversion of energy to heat.

In some embodiments the EM radiation absorbing layer is composed of a plurality of such regions. In some embodiments the EM radiation absorbing layer is made up differently (e.g. a continuous single layer or a plurality of non-concentric shapes or portions) but as an aggregate it has (or is divisible into) a plurality of concentric frame shaped regions. At times one or more of the concentric frame shaped regions may comprise or consist of one or more regions that are devoid of EM radiation absorbing layer.

These are formed so that each concentric frame shaped region has an EM radiation absorption coefficient that is greater than any other concentric frame shaped region it encloses.

In some embodiments, the concentric frame shaped regions have a shape following the contour of the antenna arms. For example, in a circular antenna the frame shaped regions may be round, while in a square antenna, the frame shaped regions may be square.

In some embodiments, in order to provide the above outlined gradual EM radiation absorption coefficient increase, the EM radiation absorbing layer may be shaped so that the amount of absorbing material increases as a function of a distance from the geometric center and/or feeding point and/or the boresight of the antenna. Additionally or alternatively, the concentration and/or density of absorbing material increase as a function of a distance from the geometric center and/or feeding point and/or boresight. Additionally or alternatively, the EM radiation absorption coefficients of the absorbing materials used in the EM radiation absorbing layer changes as a function of a distance from the geometric center and/or feeding point and/or boresight. Additionally or alternatively, the width or density of conductive element(s) of the spiral antenna changes as a function of a distance from the geometric center and/or feeding point.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIGS. 1A to 1F, which are a top view, a cross sectional perspective view and four alternative cross sectional views of an exemplary EM probe 90 having a planar or non-planar spiral antenna conductor 91 having an electromagnetic (EM) radiation absorbing layer 92 mounted along at least a portion of the antenna conductor 91 with substantially concentric frame shaped regions 93 having different EM radiation absorption coefficients, optionally around a portion 95 which is devoid of EM radiation absorbing layer or comprises a material with a lower degree of EM absorption, according to some embodiments of the present invention. Optionally, the attenuation of EM energy by an EM radiation absorbing layer does not comprise or consist of lumped elements.

The EM radiation absorbing layer 92 may be continuous and/or non-continuous so that the substantially concentric frame shaped regions 93 may be visually separated and/or continuous. In FIG. 1A an outline of an exemplary planar spiral antenna having an antenna conductor 91. The outline of each of a plurality of concentric frame shaped regions 93 is depicted in FIG. 1A by graduated tones and the borders between them are depicted by dashed lines. The level of the radiation absorption coefficient is exemplified by series of graduated tones ranging from white to dark gray (with darker tones depicting a higher level of the radiation absorption.

Figure 1A:
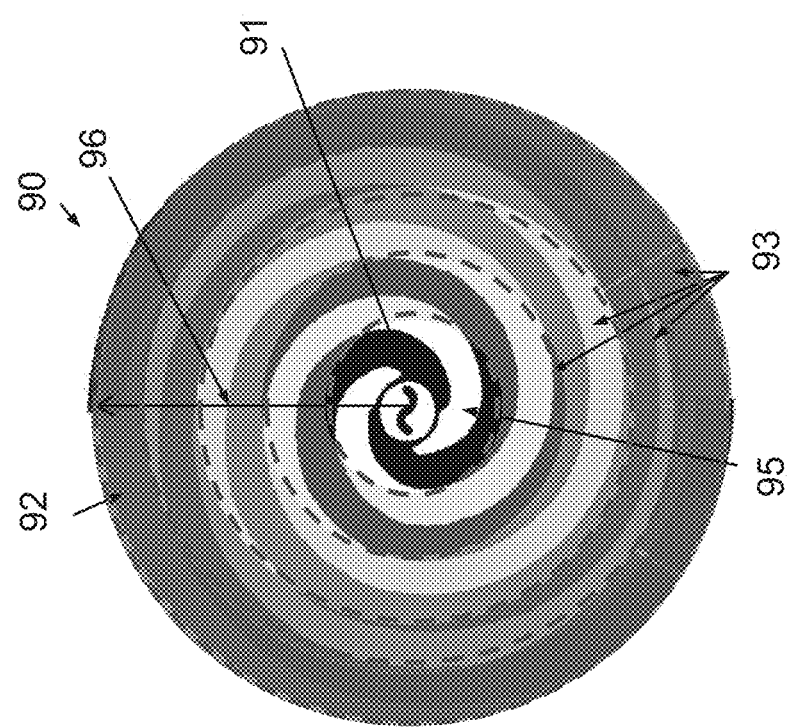
FIG. 1A is a top schematic illustration of an exemplary EM probe that includes a spiral antenna having mounted an EM radiation absorbing layer with concentric frame shaped regions having different EM radiation absorption coefficients, according to some embodiments of the present invention.

An example for concentric frame shaped regions is shown schematically in FIG. 1B. In some embodiments these regions comprise antenna conductor 91 or a portion thereof and in others they do not. As seen in FIG. 1B, the regions have a given volume. This volume may extend above and or below and/or through antenna conductor 91. The frame shaped regions may be characterized by the length occupied by each region along cross section A-B shown in FIG. 1B, and in some embodiments, this length is the same for a plurality or all frame shaped regions.

For brevity, an EM radiation absorption coefficient may be referred to as an absorption coefficient. This absorption coefficient is a quantity that characterizes the degree to which an EM radiation absorbing layer or portion thereof may attenuate EM energy that interacts therewith by conversion thereof to heat. A larger absorption coefficient means that the energy is attenuated to a greater degree as it interacts with the layer, and a smaller absorption coefficient means that the layer attenuates the EM energy to a lesser degree (if at all). The absorption coefficient is optionally measured using units of reciprocal amount (e.g. length) of the conductor of the antenna that is exposed to the EM radiation absorbing layer. In some embodiments, the radiation absorption coefficient of an EM radiation absorbing layer at a given point along an antenna is a function of the amount of EM radiation absorbing layer along an effective perimeter associated with that point, as explained in further detail below, for example with respect to FIGS. 7A and 7B.

Since in the spiral antenna each radiated frequency has its own effective radiation radius from boresight, the effective overall absorbing experiences for each frequency is different and is the integral of the absorption from the feeding point to the effective radius of radiation along the conducting arms, which is equivalent to the integral of the absorption coefficient from the feeding radius to the effective radiation radius of that frequency.

In some embodiments, the total EM radiation absorptive effect on the radiation of a given frequency is a function of the integral sum of all EM radiation absorption coefficients of the concentric frame shaped regions between the feed of an antenna and the region at which the frequency is effectively radiated or intercepted.

Optionally, the EM radiation absorbing layer comprises material (e.g. ferromagnetic material) having a high permeability loss tangent (tan $\delta=\mu''/\mu'$) that diminishes magnetic fields to a degree that is proportionate to the degree to which the EM energy is exposed to the EM radiation absorbing layer.

Optionally, the attenuation of EM energy by an EM radiation absorbing layer may be controlled by using materials having different electromagnetic properties (e.g. different permeability loss tangent), by changing the amount and/or concentration of the material(s) in the EM radiation absorbing layer and/or by changing the coverage of the antenna by the EM radiation absorbing layer (e.g. using discontinuities or volumes), etc. It is noted that for EM energy having a given frequency, discontinuities that are significantly smaller than the wavelength (<0.25 lambda or <0.1 lambda) may be used along a propagation path of the energy. In such cases the discontinuities will have an insignificant effect and only the aggregate material will have effect. In some embodiments, where there are a plurality of propagation paths for the energy, discontinuities may be chosen to be significantly smaller than the wavelength in all of the propagation paths if they are to have little to no effect.

Additionally or alternatively, the attenuation may be controlled by selecting the location of the EM radiation absorbing layer along the antenna. For example—in a spiral antenna having a plurality of arms, the same material placed between the arms of the antenna may have a stronger effect on the EM energy than it would have had if positioned above or below the antenna plane.

The EM radiation absorbing layer 92 is disposed in proximity or in contact with the antenna conductor 91. Examples for the positioning of the EM radiation absorbing layer are provided in FIGS. 1C-1F which depict some optional cross sections A-B through EM radiation absorbing layer 92.

Figure 1C:
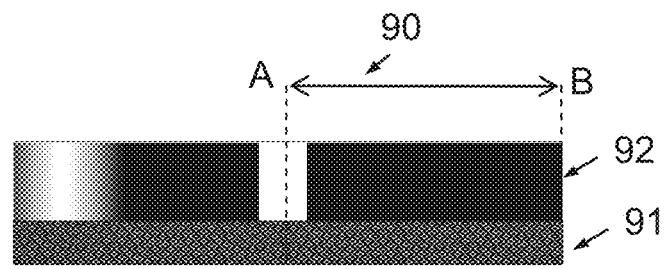
FIGS. 1C-1F are schematic lateral cross sectional illustrations of antennas having a top view essentially as shown in FIG. 1A, according to some embodiments of the present invention.
Figure 1D:
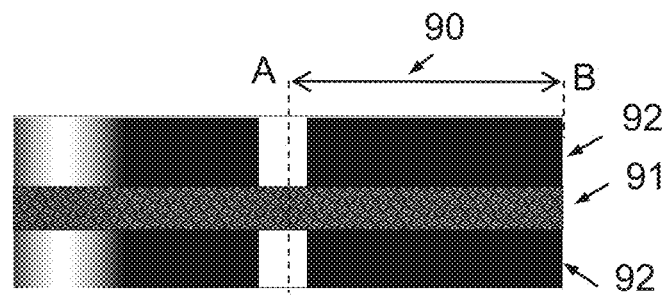

In FIG. 1C, EM radiation absorbing layer 92 is disposed along a frontal side or back side of a planar antenna having an antenna conductor 91. The frontal side is that which is perpendicular to and faces the transmission and/or reception main direction. For example, at least the frontal side of the transmitting conductive elements of the spiral antenna is at least partly covered by, coated by, taped with or attached to the EM radiation absorbing layer 92. In FIG. 1C, both the frontal and back side of the antenna are covered by EM radiation absorbing layer 92. In both FIGS. 1B and 1C the EM radiation absorbing layer 92 is shown to have a graded composition of EM radiation absorbing layer or EM absorbing material deposited therein, as depicted by the graded shading of EM radiation absorbing layer 92. FIG. 1D shows an alternative cross section, wherein antenna conductor 91 is sandwiched by or embedded within EM radiation absorbing layer 92.

Figure 1E:
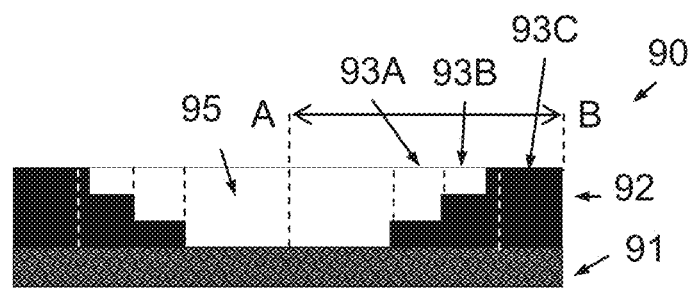

In FIG. 1D EM radiation absorbing layer 92 is shown to have a graded composition of EM radiation absorbing layer or EM absorbing material. Conversely, the cross section shown in FIG. 1E, shows a layered formation of EM radiation absorbing layer within EM radiation absorbing layer 92. As seen in this example, concentric frame shaped region 93A as shown within the cross section consists of EM radiation absorbing layer whereas concentric frame shaped region 93B is partially devoid of EM radiation absorbing layer, and innermost concentric frame shaped region 93C has the least amount of the three. The three regions are separated by dashed lines. In some embodiments, unlike the instant, concentric frame shaped regions coincide with the layers comprised in EM radiation absorbing layer.

Figure 1F:
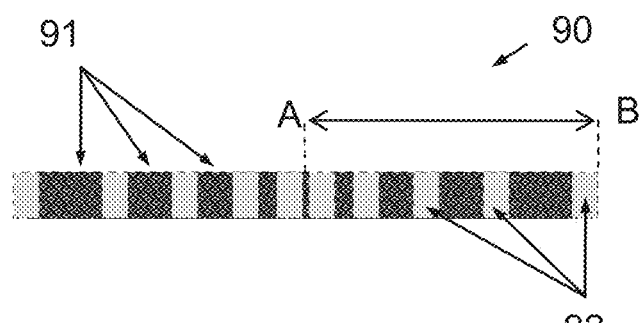

Finally, in FIG. 1F, a cross section through a spiral antenna having an antenna conductor 91 is shown. In this example, EM radiation absorbing layer 92 comprises EM radiation absorbing layer optionally embedded between with the antenna arms. The EM radiation absorbing layer is set so that if the spiral arms (e.g. conductor arms) of the spiral antenna have a fixed thickness equal length arm portions have equal loss of energy when free from the EM radiation absorbing layer 92.

The EM radiation absorbing layer 92 is optionally made of an EM absorbing material. As further described below, the EM absorbing material is optionally distributed in the EM radiation absorbing layer 92 so that the absorption coefficient of the concentric frame shaped regions 93 increases when moving away from the boresight of the antenna, to its edges along the antenna's cross section A-B.

Optionally, the EM absorbing material comprises a material that induces a dissipation of EM energy and currents, for example one or more materials such as ECCOSORB® material of Emerson & Cuming®, with a permeability loss tangent (tan $\delta=\mu''/\mu'$)>0.01, >0.1 or >0.3 or >0.6, where $\mu''$ denotes imaginary part of magnetic permeability and $\mu'$ denotes a real part of the magnetic permeability, for all or some of the frequencies within the range of 100 Megahertz (MHz)-5 Gigahertz (GHz) for example for 1 GHz and/or 2 GHz and/or a permittivity loss tangent (tan $\delta=\varepsilon''/\varepsilon$)>0.01, >0.1 or >0.3 or >0.6, where $\varepsilon''$ denotes imaginary part of electric permittivity and $\varepsilon'$ denotes real part of the electric permittivity, for all or some of the frequencies within the range of 100 MHz-5 GHz for example for 1 GHz and/or 2 GHz. Optionally, the EM absorbing material is characterized by $\mu'$ in the range between 1 and 30, for example around 20, and/or $\mu''$ in the range between 1 and 30, for example in the range between 6 and 15, and/or characterized by $\varepsilon'$ in the range between 2 and 60, for example in the range between 8 and 30 and/or $\varepsilon''$ is in the range of 1-30 for example 5-10. This for all or some of the frequencies in the range between 100 MHz and 5 GHz for example in the range between 8$\varepsilon\varepsilon\varepsilon$00 MHz and 3.6 GHz. In some embodiments, the EM absorbing material comprises a material selected according the frequency of EM energy that is to be affected. In some embodiment a carrier, like silicon or other polymer material, can be mixed with one or more of the following: ferromagnetic materials, materials with different dielectric properties like fluids, oxidized metals, resistive conductors, where the mixing can be such to have different profile EM characteristics such as different absorbing coefficient over different distanced from boresight with continuous changing EM coefficient. Optionally, the EM absorbing material is selected to best attenuate EM energy at least in frequencies that are transmitted by the external portions of the antenna. For example this may be the part at the periphery of the spiral antenna that spans 64% or less of the total surface area of the antenna, or even or the external 36% or less of the surface or even 19% or less of the radiating surface area. In a round spiral antenna, for example, this may be the external 40% of the radius of a round antenna, or the external 20% or even the external 10% or less of the radius of a round antenna.

Optionally, as shown for example in FIG. 1F, the EM radiation absorbing layer 92 fills spaces in the plane of the antenna conductor 91 of antenna, for example gaps between conductive elements, such as arms. Optionally, the EM radiation absorbing layer 92 fills a space between the plane of conducting line(s) of the antenna and a ground plane. In some embodiments, the antenna has a single conducting line, for example a one-arm spiral antenna having a ground plane with a circular or a rectangular shaped conductor running in parallel to the ground plane. This line is considered as a micro-strip where the spiral conductor and the ground plane are separated by a substrate. In such embodiments, the EM radiation absorbing layer 92 has a substantial effect when it is between the conducting line and the ground plane.

The construction of the EM radiation absorbing layer 92, as described above, may provide an increase of the effective and usable bandwidth of the antenna in a given size. Specifically, it may enable a lower cutoff frequency with improved smoothness of the lower band while at the same time maintain high efficiency of the higher band and a smooth transition from the lower band to the higher band, for example fewer notches and smooth spectrum behavior of both phase and amplitude response of the antenna.

The EM radiation absorbing layer 92 can be designed in multiple configurations to achieve different performance tradeoffs. For example, increasing the ratio between the antenna area the EM radiation absorbing layer 92 covers and the antenna area that is not covered with it, increases the effect of the EM radiation absorbing layer 92. In particular, such a ratio increases the smoothness of the frequency response in lower frequencies in addition to lowering of low cutoff frequency and improving circular polarization in low frequencies but trading efficiency in lower frequency in return On the other hand, a ratio increase reduces the efficiency of the transmission in high frequencies that now have their radiation areas covered by absorbing material.

Figure 7A:
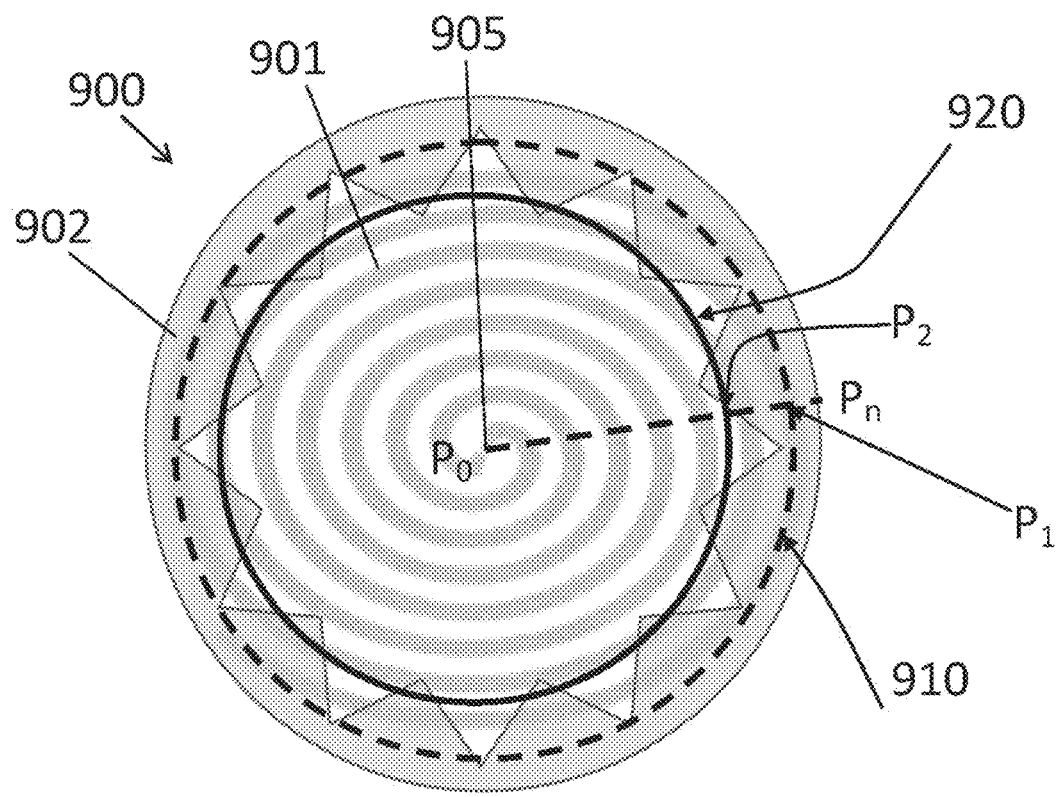
FIGS. 7A and 7B schematically depict EM probes having an EM absorbing substrate, where
Figure 7B:
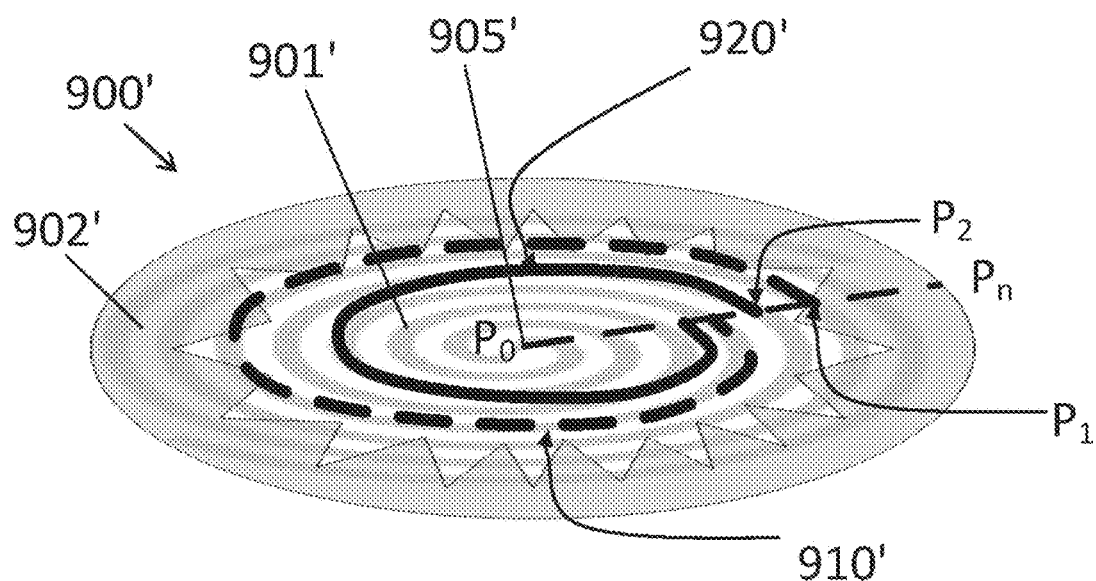

Attention is drawn now to FIGS. 7A and 7B. As depicted in these drawings, any point on an antenna may have an effective perimeter associated with it. In some embodiments, the radiation absorption coefficient of an EM radiation absorbing layer at a given point is a function of the amount of EM radiation absorbing layer along the effective perimeter associated with that point. In some embodiments, the radiation absorption coefficient of an EM radiation absorbing layer at each of the concentric frame regions is a function of the integral sum of the amount of EM radiation absorbing layer along a plurality of effective perimeters associated with each region. In some embodiments, the radiation absorption coefficient of an EM radiation absorbing layer of a concentric frame region is a function of the integral sum of the amount of EM radiation absorbing layer along all effective perimeters from the feed of the antenna and up to the effective perimeter of the region that is furthest away from the feed.

The effective perimeter may, in some embodiments, be a region of an antenna that radiates a given frequency or band of frequencies at a maximum or near maximum efficiency. In a spiral antenna the active region is the part of the antenna from the feed and up to a place on the antenna where the circumference of the spiral equals the wavelength. In some embodiments this also includes parts of the spiral that have radiuses that differ from the radius of the aforementioned circumference by up to 10% or up to 20% as measured from the feed of the antenna.

It is noted that for EM energy having a given frequency, discontinuities that are significantly smaller than the wavelength (<0.25 lambda or <0.1 lambda) may be used along a propagation path of the energy. In such cases the discontinuities will have an insignificant effect and only the aggregate material will have effect. In some embodiments, where there are a plurality of propagation paths for the energy, discontinuities may be configured to be significantly smaller than the wavelength in all of the propagation paths if they are to have little to no effect.

FIG. 7A depicts for example EM probe 900 comprising a round spiral antenna 901 having EM radiation absorbing layer attached thereto as EM radiation absorbing layer 902. Antenna 901 has a cross section from point $P_0$ to point $P_n$ spanning between point 905 ($P_0$ which may be the feed, geometric center and/or boresight of antenna 901) and a point $P_n$ on the external edge of the antenna. At any point along that cross section (shown for example $P_1$ and $P_2$) the effective perimeter (910 and 920, respectively) is the circle around the feed 905 at a fixed distance ($P_1$ or $P_2$, respectively) from point 905. Optionally the effective perimeter includes parts of the antenna having a radius that is from 10% or 20% shorter than $P_1$ (or $P_2$ as the case may be) to parts of the antenna having a radius that is from 10% or 20% shorter than $P_1$ (or $P_2$, respectively). In some embodiments, when a frequency (or band of frequencies) is radiated at maximum efficiency from a plurality of regions between two points (e.g. $P_1$ and $P_2$) along the cross section, the effective perimeter may consist of the entire antenna surface between the effective perimeters of the two points (in this example, between 910 and 920).

FIG. 7B depicts for example EM probe 900' comprising an oval spiral antenna 901' having EM radiation absorbing layer attached thereto as EM radiation absorbing layer 902'. Antenna 901' has a cross section $P_0$-$P_n$ spanning between point 905' ($P_0$ which may be the feed, geometric center and/or or boresight of antenna 901') and a point $P_1$ on the external edge of the antenna. At any point on a cross section (shown for example $P_1$ and $P_2$) the effective perimeter (910' and 920', respectively) is a 360° path leading backwards along an antenna arm from the given point on the cross section towards point 905'. In some embodiments, when a frequency (or band of frequencies) is radiated at maximum efficiency from a plurality of regions between two points (e.g. $P_1$ and $P_2$) along the cross section, the effective perimeter may consist of the entire antenna surface between the effective perimeters of the two points (in this example, between 910 and 920).

According to some embodiments of the present invention the antenna is a planar spiral antenna. For example, reference is now made to FIGS. 2A-2B, which are lateral and top schematic illustrations of an exemplary EM probe 300 having a round spiral antenna having a conductor 302, 305 mounted so that one side thereof (e.g. the front) faces an EM radiation absorbing layer 306, 301.

The spiral EM probe 300 comprises a conductor 302, 305 shaped for example as a single spiral arm or a plurality of spiral arms having a common source which functions as a feeding point 303. The spiral EM probe 300 may be an Archimedean spiral antenna, or an equiangular spiral antenna of any shape, including for example a square spiral antenna, a circular spiral antenna and an oval spiral antenna. The spiral antenna conductor 302, 305 may be planar or shaped to form a three dimensional structure for example a conical spiral antenna or a horn antennas with spiral tapering on its walls, and/or the like. Optionally, the spiral antenna conductor 302, 305 is printed on a dielectric medium (shown in FIG. 2A as dielectric material layer 304), optionally with a specific permittivity and dimensions. An antenna may be deemed to comprise both the conductor 302, 305 and the dielectric material 304. For example, the dielectric medium is made of Rogers R3010™.

Figure 2A:
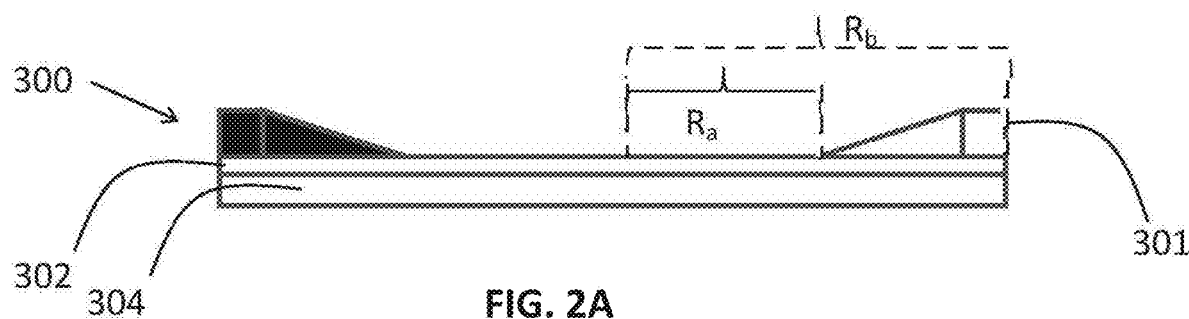
FIGS. 2A-2B are lateral and top schematic illustrations of an exemplary EM probe having a spiral antenna mounted so that one side thereof faces an EM radiation absorbing layer, according to some embodiments of the present invention.
Figure 2B:
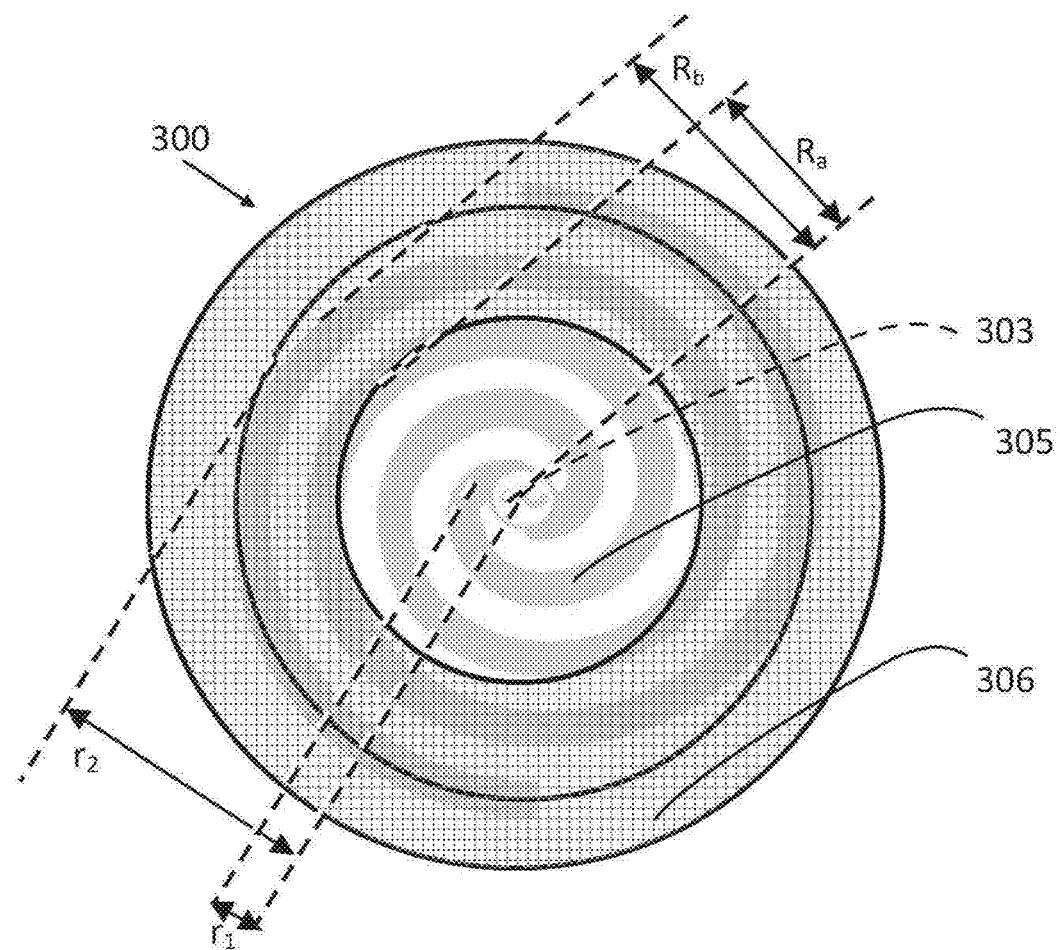

In a spiral antenna, for example as depicted in FIG. 2B, the inner radius ($r_1$ is measured from center of the spiral to the center of the first turn while the outer radius ($r_2$) is measured from center of the spiral to center of the outermost turn. In such antennae, $f_{low}=c/(2\pi r_2*sqrt(|\epsilon''\mu''|))$ may denote an approximation of the lowest operating frequencies of the spiral antenna and $f_{high}=c/(2\pi r_1*sqrt(|\epsilon'\mu'|))$ may denote an approximation of the highest operating frequencies where c denotes speed of light and $\epsilon'$, $\mu'$, denote the effective complex dielectric permittivity and permeability constant, respectively in the vicinity of the inner radius of the spiral antenna and $\epsilon''$, $\mu''$, denote the effective complex dielectric permittivity and permeability constant, respectively in the vicinity of the outer radius of the spiral antenna. In an rθ coordinate system, the spiral grows along r-axis and θ-axis simultaneously.

Figure 2C:
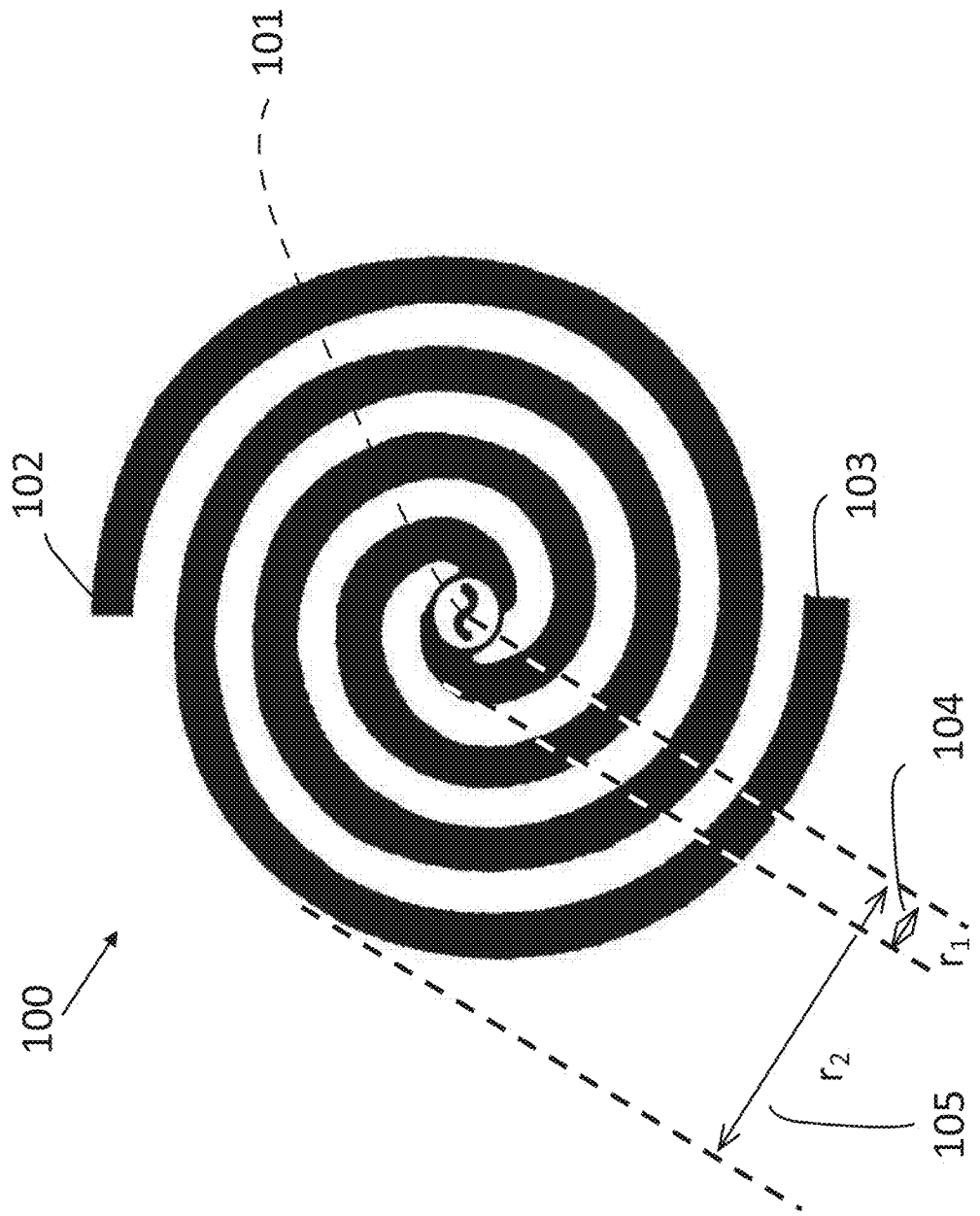
FIG. 2C is a schematic illustration of an exemplary spiral antenna without a radiation absorbing layer.

FIG. 2C depicts an exemplary spiral antenna 100 without a radiation absorbing layer. In FIG. 2C an exemplary two arm spiral antenna 100 is depicted. A feeding point 101 of the antenna 100 is in the geometric center of the structure where the EM energy propagates along conductive arms 102, 103. Characteristic radii 104 and 105 are marked by $r_1$ and $r_2$ respectively and govern the highest and lowest characteristic frequencies of the antenna.

The spiral shaped conductor windings may be laid over non planar surfaces (inside or outside), for example over a three dimensional (3D) structure having any of various shapes and dimensions, for example a cone and a pyramid, for instance a spiral shaped conductor winding has a conical log spiral antenna model 3102 from ETS LINDGREN™.

Optionally, the radiation absorbing layer 306, 301 (FIG. 2A and FIG. 2B) is placed, for example laminating, coating, and/or otherwise attached to the spiral antenna 302, 305. In such embodiments, the permittivity and permeability of the different regions of radiation absorbing layer 306, 301 affect the manner EM energy spreads in the antenna, for example in the spiral path along the conductive transmission lines of the in spiral antenna 302, 305. In some embodiments, the level of absorption of EM energy increases with the traveled distance along the absorbing layer 306, 301. As described in the example above, the absorbing layer 306, 301 is designed so that the outer peripheral windings of the spiral have higher attenuation effect by the absorber material. This may be achieved for example by increasing the total amount of EM radiation absorbing layer along a given path.

In some embodiments this is achieved at least by increasing the coverage percent as the traveling distance increases. In some embodiments this effect is measured along an energy propagation path on a conductive portion of the antenna (e.g. along a spiral arm of the spiral antenna). In some embodiments this is achieved by having a higher amount of EM radiation absorbing material placed on an effective perimeter associated with a first point on an antenna cross section than is placed on an effective perimeter that is associated with a second point on the cross section where the second point is closer to the antenna boresight than the first point).

In some embodiments, the layer of absorbing material is configured (e.g. sized and/or shaped and/or distributed along the antenna) while taking into consideration other properties of the spiral antenna that affect the propagation of EM energy in the antenna. Examples for such properties include antenna architecture and design features (e.g. width and/or density of conductive element(s) of the antenna that may change as a function of a distance from the geometric center and/or feeding point, for example the distance between any two adjacent arms in the spiral antenna).

Since in some embodiments the material is agnostic to the direction of the propagation of the EM radiation in the transmission lines it absorbs this radiation on its way to the end of the propagation path along the antenna, and on its way back once reflected from the end. Reflected energy from the end of the antenna may add radiation which interfere and destruct the radiation emitted, resulting in non-smooth spectral and polarization behavior. The reduction in reflected energy power at lower frequencies may move the low cutoff frequency to lower frequencies due to a lesser effect of destructive interference. The reduction in reflected energy power at all frequencies may smoothen the frequency response otherwise having ripples and notches due to interference effects due to reflected energy (e.g. alternating destructive and constructive frequencies).

Optionally, the EM radiation absorbing layer is positioned such that in the one or more innermost concentric frame shaped regions a relatively small portion of the EM energy is absorbed, said portion of the radiation being significantly smaller than the part of the conducting surface of the antenna that is associated with these one or more innermost concentric frame shaped regions. Optionally, such one or more innermost concentric frame shaped regions are associated with no EM radiation absorbing material and/or are associated with no part of the EM absorbing layer. For example, along the line $r_2$ extending from the center of feed 101 of spiral antenna 92 in FIG. 2C (or boresight or geometric center of the antenna) and to the external edge of the spiral arms, the innermost concentric frame shaped regions may be associated with the inner 30% or more (or even 50% or more or 70% or more) of the radius (as measured from point 101 outwards). Optionally, the innermost concentric frame shaped regions may be associated with the inner 10% or more of the surface of the antenna conductor, or with the innermost 25% or more of the conductor or even with the innermost 50% or more of the conductor). Such innermost concentric frame shaped regions may be configured to absorb only 5% or less of the total amount of EM radiation absorbed by the EM radiation absorbing layer, or 10% or less of the EM radiation or 25% or less of the EM radiation, as detailed in Table 1.

TABLE 1

| Inner shape area (% of antenna area) | Amount absorbed (% of total absorbance) |
| --- | --- |
| 10 or more | 5% or less |
| 25 or more | 10% or less or 5% or less |
| 50 or more | 25% or less or 10% or less or 5% or less |

Optionally this is measured at least or only for the frequencies of EM energy that are radiated most efficiently from the outermost concentric frame shaped regions of the antenna, spanning for example the outermost 40% or less of the radius or even 20% or less or 10% or less of the radius. Optionally this is measured at least or only for the frequencies of EM radiation that are radiated most efficiently from the outermost concentric frame shaped regions of the antenna, spanning for example the outermost 64% or less of the surface area or even 36% or less or 20% or less of the surface area of the antenna conductor that is associated with the concentric frame shaped regions. Optionally, the innermost concentric frame shaped regions that are associated with the inner 50% or more of the surface of the antenna conductor, or with the innermost 25% or more of the conductor or even with the innermost 10% or more of the conductor) have no EM radiation material associated with them.

Optionally, each of the concentric frame shaped regions other than the innermost concentric frame shaped regions have an equal or a higher radiation absorption coefficient than a concentric frame shaped region it frames, while each of the innermost concentric frame shaped regions has an equal radiation absorption coefficient than a concentric frame shaped region it frames.

With reference to FIGS. 1A-1F, the EM radiation absorbing layer 92 covers, for example coats, laminates, tapes, and/or attaches to antenna conductor 91 where the respective effect of the EM absorbing material in the volume of different regions 93 has a varying profile (optionally increases) along the entire path 96 (or along an effective perimeter for given points along path 96) as the distance from the geometric center of the antenna increases.

Additionally or alternatively, the thickness of the EM radiation absorbing layer 92 along the path 96 may have a varying profile (e.g. increase) as a function of the distance from the feeding point 303 of an antenna (or for a portion thereof), for example as depicted in FIGS. 2A and 2B along the line $R_b$. The EM radiation absorbing layer 301 is layered above the layer comprising the conducting spiral arms 302, which in turn is layered above a dielectric material layer 304. Areas having a distance of Ra or less from the feeding point 303, such as point 305, are not covered (or are covered with material without a significant absorption effect) and areas having distance of Rb and over, such as point 306, are covered by the layer with maximum thickness.

The increase in thickness may achieved for example by layering rings having an increasing cutout diameter, creating a step like cross section (e.g. FIG. 1E), and/or by having the EM absorbing material formed as a single layer that thickens as the distance from the feeding point increases and/or by having a varying concentration of absorbing material (e.g. FIGS. 1C and 1D).

Optionally, discontinuities are created in the EM radiation absorbing layer 301 by this structure in dimensions set relative to the EM radiation wavelengths, for example similarly to the described below. The discontinuities may be smaller than the typical wavelength propagating through them (e.g. patterns of EM radiation absorbing layers shown in layer 202 of FIG. 3A or in FIGS. 3C, and 7A). For example, dimensions of the discontinuities are smaller than a quarter of the wavelength and/or a slope that increases in thickness, for example, at a rate of a quarter of a wavelength or less for each unit of length equal to the wavelength (in the propagation direction). Additionally or alternatively, with reference to FIGS. 1A, 1C and 1D, the EM radiation absorbing layer 92 comprises absorbing material concentration that is determined as a function of the distance from the feeding point, boresight or geometric center of an antenna. Increasing the concentration of absorbing material can be achieved by grading of the material concentration.

Additionally or alternatively, the EM radiation absorbing layer 92 comprises a composite material where the share of the absorbing material in the composite material is gradually increased along the path 96. For example, one may embed a ferromagnetic compound with a controlled and varying concentration within a carrier (e.g. a rubber or any polymer). Optionally, a dielectric material used in the construction of the antenna 90 and the EM radiation absorbing material is integrated into the composite material. In such embodiments, the EM radiation absorbing material may be added to the dielectric material during the early construction stages. In a spiral antenna, the composite material and/or the EM radiation absorbing material is laid along the antenna (e.g. along an energy propagation path and/or a spiral arm and/or along path 96) with increasing coverage. This can be achieved by different patterning of the absorbing material layer (which comprises the composite material), for example as described below.

Optionally, the EM radiation absorbing layer 92 has gaps wherein absorbing material is not present. Optionally, the pattern is designed so that discontinuities along a path are formed in dimensions set relative to the EM radiation wavelengths. For example, the discontinuities are smaller than a quarter of a wavelength which is designed to propagating therethrough so as to have little or no effect on the propagating wave. Optionally, the reduced effects are of reflections smaller in power relative to the power of the main propagating signal by at least a factor of 2. The discontinuities optionally increase in size along the propagation path 96.

Figure 3A:
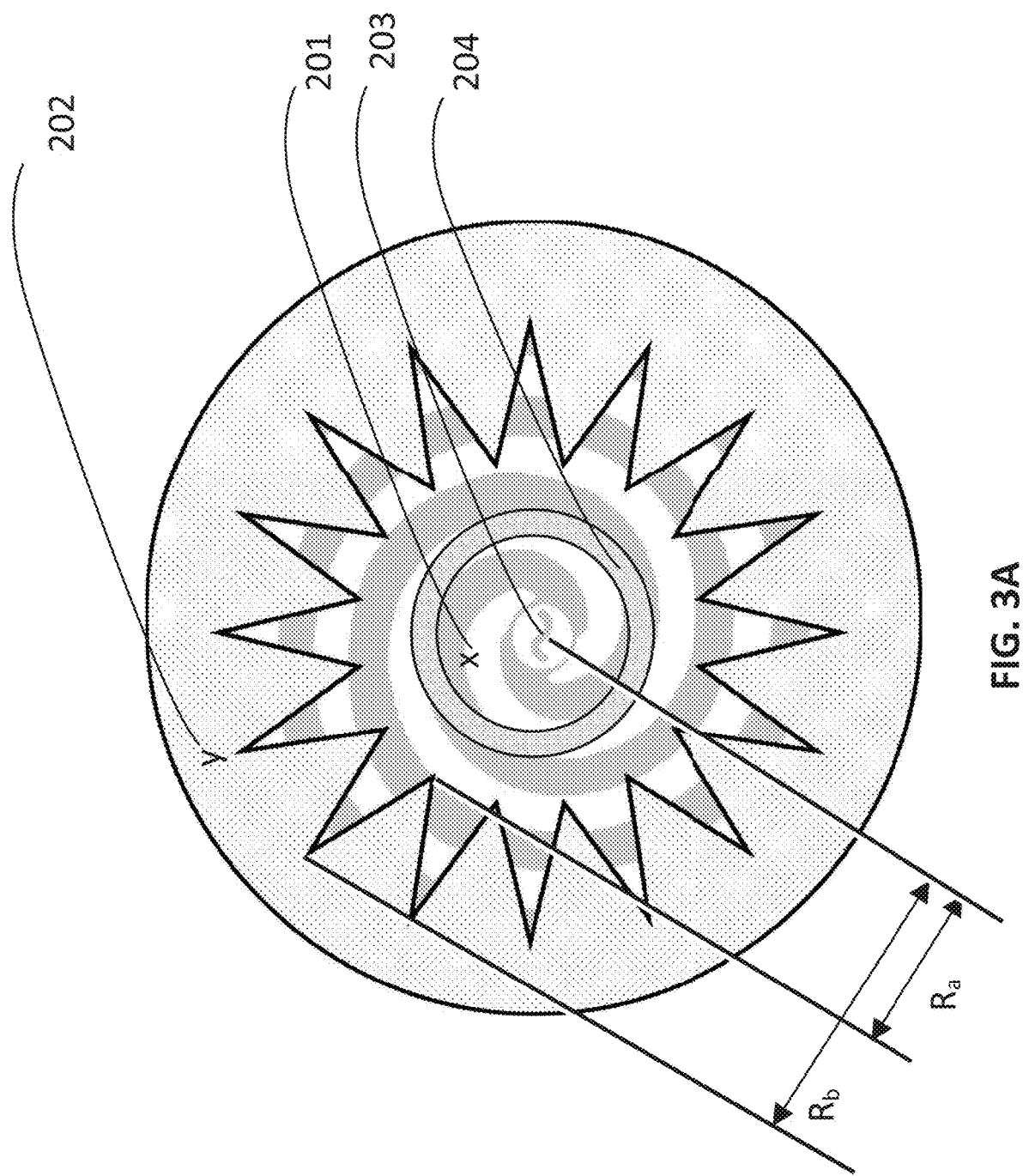
FIG. 3A is a schematic illustration of an EM probe having an EM radiation absorbing layer with a star shaped cutout, according to some embodiments of the present invention.

According to some embodiments of the present invention, the EM radiation absorbing layer 92 is shaped such that less EM radiation absorbing material is present in regions which are closer to the feeding point. For example, the EM radiation absorbing layer 92 has a pattern wherein spikes facing an aperture in front of feeding point of the antenna conductor 91. For example, FIG. 3A schematically depicts an EM probe 200 having an EM radiation absorbing layer 202 with a star shaped cutout constructed in front of the arms 201 of a spiral antenna. The star shaped cutout may comprise material having lower radiation absorption properties than the outer portion of the layer (e.g. a reduced concentration of absorbing material) or be left empty. EM energy advancing from marked point X to marked point Y on a spiral propagation path of the spiral arms encounters noncontiguous sections of the EM radiation absorbing layer 202 so that the area through which the spiral path passes is covered with increasing amount of absorbing material. Areas having a distance of $R_a$ or less from feeding point 203, for example point X, are not covered. Areas having distance of at least $R_b$, for example point Y, are completely covered. A similar effect may be achieved using a plurality of distinct patches rather than a continuous layer, as exemplified in FIG. 3C. The gradual tapering in the design of the EM radiation absorbing layer 92 may be configured to avoid or reduce reflection and/or ringing that may result from the EM energy's response to abrupt impedance changes. The perceived impedance along an energy propagation path (e.g. along path 96 in FIG. 1 and/or along a spiral arm of the spiral antenna) is dependent on the frequency (or wavelength) of the energy, and is averaged according to the media encountered. Small gaps (relative to wavelength; e.g. 0.25 lambda or less) along the propagation path thus do not cause reflection and/or ringing and therefore make the spectrum smoother.

The shape of the EM radiation absorbing layer 92, specifically the lower density of the absorbing material in areas closer to the feeding point or boresight of the antenna conductor 91 allows a relatively low attenuation of energy having higher frequencies. For example energy that is effectively radiated from within the area defined by a circular circumference having a radius $R_a$ and a center at the boresight or feeding point of the antenna has frequencies $f>c/(2\pi R_a*sqrt(|\epsilon\mu|))$ where c denotes a constant of light speed, $\epsilon$ and $\mu$ denotes effective complex dielectric and permeability constants, respectively. In this example, $R_a$ also denotes a radius of the smallest circle about the feeding point or boresight of the antenna conductor 91 having some part of it covered by absorbing material. In some embodiments shape of the EM radiation absorbing layer 92 (and/or its material) may be selected so as the attenuation of the aforementioned frequencies f will be no greater than 5 decibel (dB) or no greater than 7 dB in relation to an EM probe with a similar antenna conductor 91 without the EM radiation absorbing layer 92. This may allow broadening of the effective bandwidth of the antenna by lowering the low cutoff frequency while maintaining minimal effect on the high portion of the band typical of the antenna. This may be significant for example when considering applications where penetration through a high loss material is required and where typically higher frequency experiences a higher loss.

Optionally, in the spiral antenna (e.g. a round spiral antenna), the coverage area of the EM radiation absorbing layer 92 extends in the radial direction and forms a cyclic pattern along the radial axis. For example, a pattern having 4 or 6 or 8 or 12 triangular areas, or more, creates a cycle that is a quarter of the wavelength or less for all frequencies radiated from the antenna (this is due to the fact that the spiral antenna has a property of radiating a given wavelength from the circular area centered around the feeding point of the antenna, and having the circumference that is equivalent to that wavelength).

According to some embodiments of the present invention, the spiral antenna is a portion of a larger antenna. For example as shown in FIG. 3A, a spiral antenna may be a part of an antenna that surrounds an inner portion (here shown as an optional ring shape 204 and the portion of the antenna that is enclosed by ring 204). Ring shape 204 may in some embodiments comprise EM radiation absorbing material. In some embodiments, the antenna may be an inner portion of a larger antenna. For example, arms 201 may exceed the area that is covered by EM radiation absorbing layer 202 (not shown). In such cases, the antenna may be limited to a portion that is within the circumference of EM radiation absorbing layer 202.

Figure 3B:
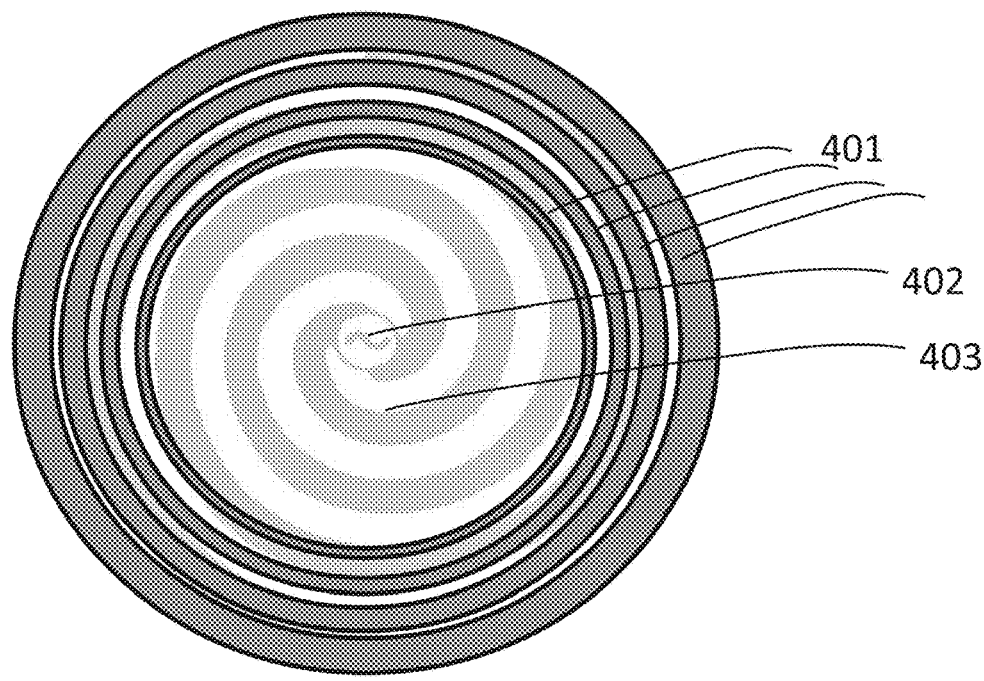
FIG. 3B is a schematic illustration of an EM probe having an EM radiation absorbing layer that comprises a plurality of concentric frame shaped layer segments increasing in width as a function of a distance from the center, for example from a boresight of the antenna, according to some embodiments of the present invention.

Additionally or alternatively, as depicted in FIG. 3B, the EM radiation absorbing layer comprises a plurality of concentric frame shaped layer segments 401, optionally annular, increasing in width as a function of a distance from the center, for example from a feeding point. Though annular frame shaped layer segments 401 are depicted in FIG. 3B, any other pattern having the property of material density that is growing as the distance from the feeding point of the antenna increases can be used. The characteristic dimensions describing the pattern discontinuities should be much smaller than the wavelengths of the radiation launched from the covered areas dimensions of discontinuities at a distance of R from the feeding point and/or along an energy propagation path along an arm of the antenna should be significantly smaller than $2\pi R$ (where $\pi$ is the radio of the circumference and diameter of a circle) to the extent that they do not cause significant reflections and/or ringing along an EM energy propagation path at least not in desired frequencies (frequencies or band of frequencies used) (e.g. reflections smaller by at least a factor of 5 or more in amplitude relative to the amplitude of the main propagating signal).

According to some embodiments of the present invention, the spiral antenna is shaped so that the frontal side thereof is non-planar, for example a spiral antenna having a three dimensional (3D) structure, optionally conical. In such embodiments, the EM radiation absorbing layer may coat the surface of the frontal side in a manner that assures that the concentric frame shaped region of the EM radiation absorbing layer are order so that a concentric frame shaped region has an equal or a higher radiation absorption coefficient than a concentric frame shaped region it encircles. Optionally, the density of the EM radiation absorbing material in the EM radiation absorbing layer is increased by distributing small amounts of the material over the surface with increasing proximity among them (e.g. a jagged configuration) and/or by using a composite material in which the concentration of the absorbing material increases.

Figure 4:
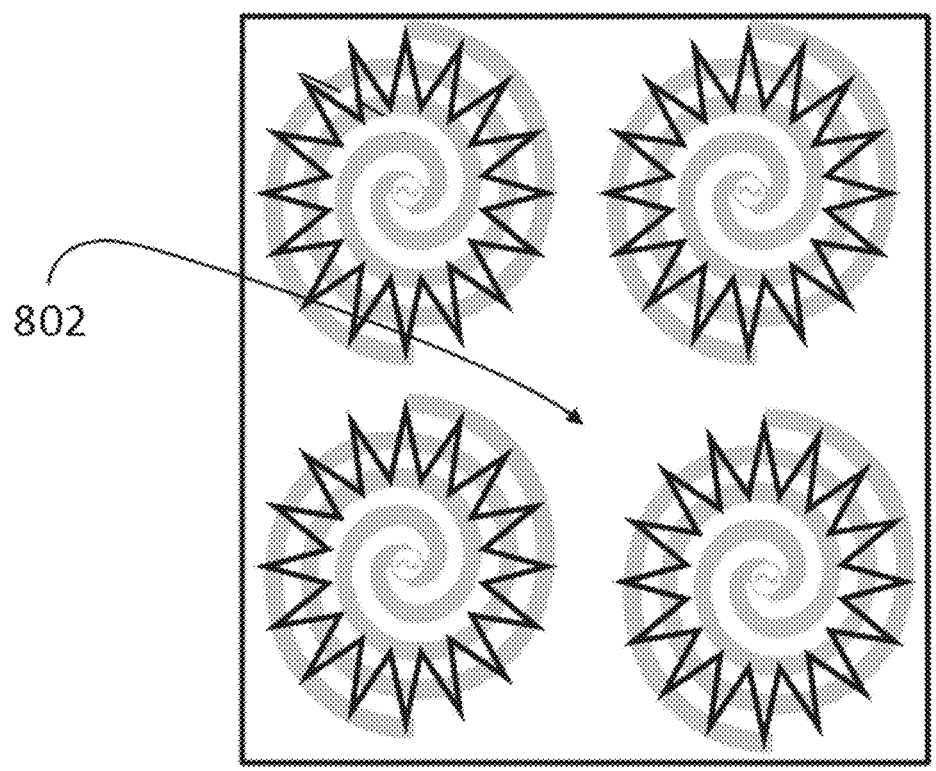
FIG. 4 depicts an optional array configuration of spiral antennas, according to some embodiments of the present invention.

According to some embodiments of the present invention, a number of EM probes as defined above, for example EM probes with planar spiral antennas, as depicted in FIG. 4, construct an array configuration. The array can be fabricated for example using an EM radiation absorbing layer 802 having a single layer of absorbing material with a pattern (or composition pattern) that maintains, per EM probe, a plurality of concentric frame shaped regions in which at least one concentric frame shaped region has a higher radiation absorption coefficient than a concentric frame shaped region it encloses. For example, a star shaped cutout 802 may be formed in the radiation absorbing layer at each spiral antenna, which cutout may comprise material having lower radiation absorption than the outer portion of the layer or be left empty. Optionally, each of the plurality of concentric frame shaped regions has an equal or a higher radiation absorption coefficient than a concentric frame shaped region it encloses.

According to some embodiment of the present invention, the spiral antenna is placed in an isolating cup shape structure, for example as described in International Patent Application No. PCT/IL2011/050003, filed on Nov. 3, 2011, and published as WO/2012/059929, which is incorporated herein by reference. Such an antenna may be used for example in biological applications where the antenna is used to couple EM energy effectively into a human or animal body or other applications where the energy is to be coupled into a medium with dielectric properties for example a medium with a dielectric constant of around 10. Other constructions, for example constructions of planar configurations described in the embodiments below, can be used.

Figure 3C:
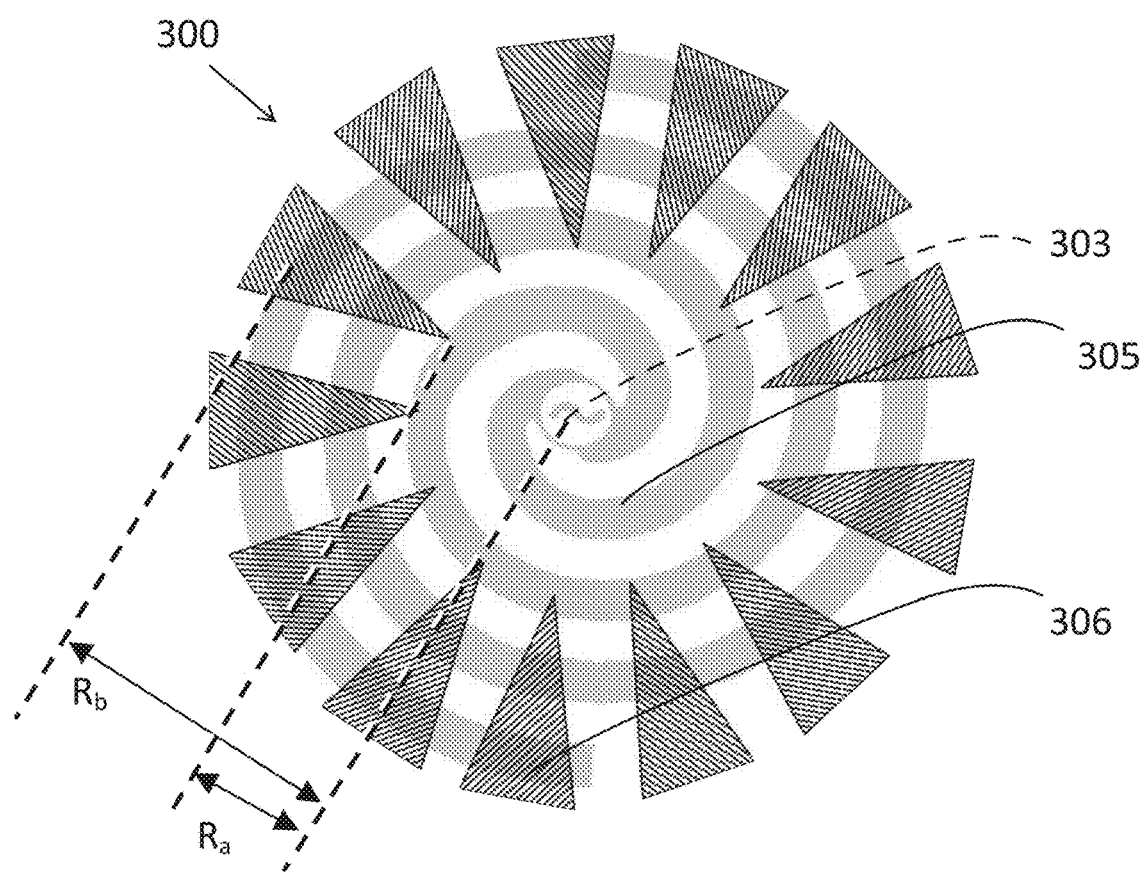
FIG. 3C is a schematic illustration of an EM probe having a plurality of triangle shaped EM radiation absorbing layer portions positioned around the periphery of the antenna, and that together comprise a plurality of concentric frame shaped segments having an increasing amount of EM radiation absorbing layer as a function of a distance from the center, for example from a boresight of the antenna, according to some embodiments of the present invention.
Figure 5:
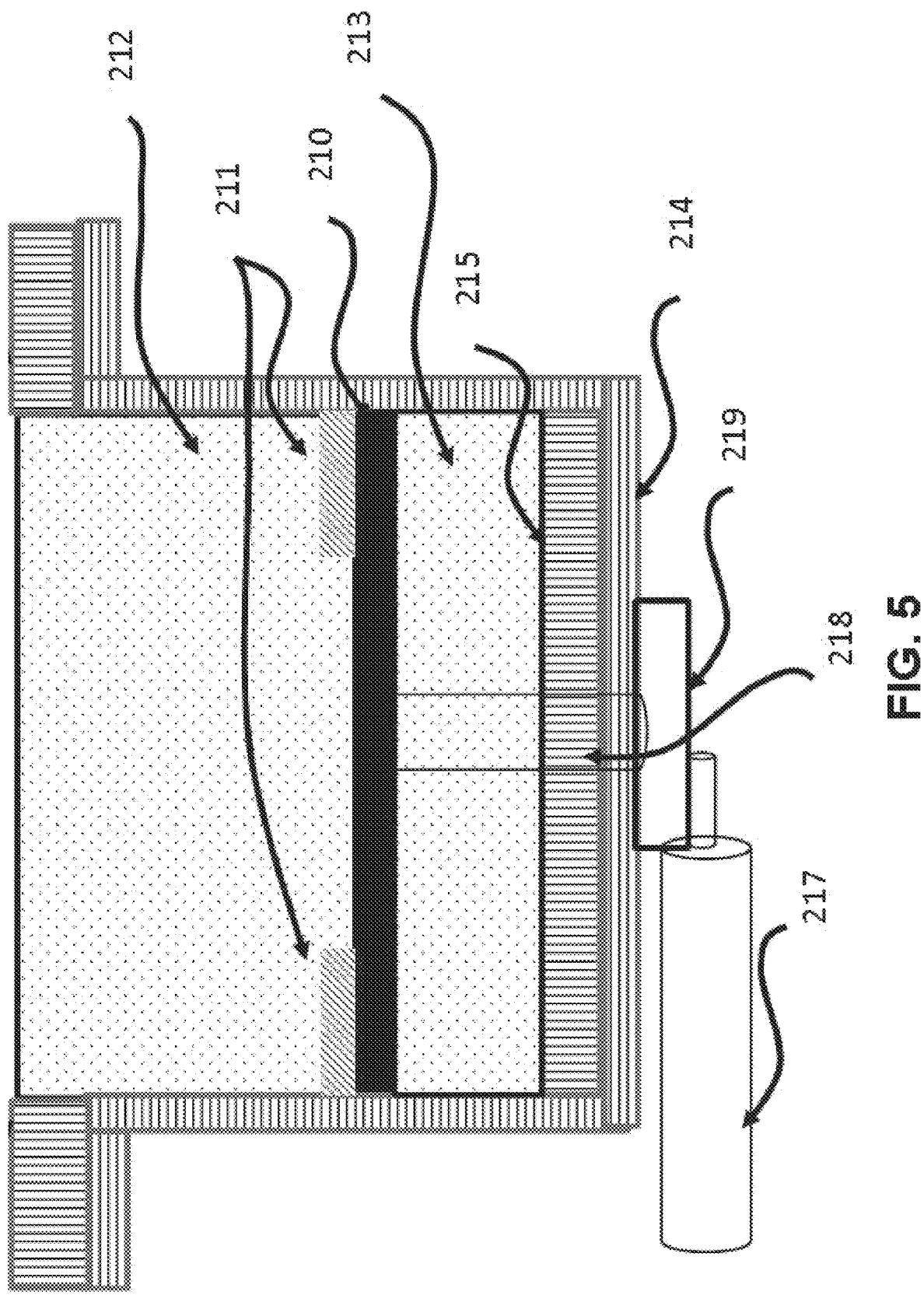
FIG. 5 is a lateral schematic illustration of a cross section of a planar antenna within a housing, the antenna covered with an EM radiation absorbing layer, for example as depicted in FIGS. 3A-3C above, according to some embodiments of the present invention.

For example, FIG. 5 is a lateral schematic illustration of a planar antenna 210, for example a 2-arm or 4-arm spiral antenna, covered with an EM radiation absorbing layer 211, for example as depicted in FIGS. 3A-3C above, according to some embodiments of the present invention. A superstrate layer 212 of dielectric material, for example 10 mm Roger RO3010 or TMM Duroid, is placed in front of the EM radiation absorbing layer 211 and optionally in the feeding aperture that is formed at its center. Another superstrate layer 213, with similar or different dielectric material, may be mounted in the back of the antenna 210. The antenna 210, dielectric material 211, 213 and the EM radiation absorbing layer 211 are contained in a conducting cup shaped cavity 214, optionally having a flange around its opening, which is optionally at least partly covered with an EM radiation absorbing layer 215. The EM radiation absorbing layer 215 covers the bottom of the conducting cup shaped cavity 214, the outside and/or the internal walls of the of the cavity 214 to suppress currents on the cavity which reflects the EM field back toward the opening of the cavity, cancelling desired field, see International Application No. PCT/IL2011/050003, and published as WO2012/059929, which is incorporated herein by reference. The EM radiation absorbing layer 215 on the flange may reduce or eliminate EM fields and/or currents conducted on the inner side of the cavity that may radiate to the outside as well as for improving isolation of the inner cavity by reducing or eliminating EM fields and/or currents induced from the outside of the cavity. Optionally, the EM radiation absorbing layer 215 may also be deployed on the outside of the cavity (not shown) for reducing currents conducted on the external side of the cavity that reduce isolation between inside of the cavity and the outside of the cavity.

Such reduced isolation may increase when a cable 217, connected to the antenna, carries induced currents serving as radiating element and/or conducting radiation between a transmitting and receiving antennas in multiple antenna configurations. FIG. 5 also describes a feeding element to the antenna 218 and an optional Balun 219 and/or other circuitry, if required, to convert the signal from the cable 217 to the feeding element 218.

Optionally, any of the above described EM probes is used in applications where the EM probe is in touching proximity to a target medium of a given dielectric, for example a human or animal body in biological sensing applications (either directly or through a thin layer, for example such as clothing). For these uses an extra layer of dielectric superstrate material, such as 212 in FIG. 5 may be added. This may enable better decoupling of the antenna from its surrounding by increasing the gap between the antenna's radiating element and the target material.

Cavity 214 may affect EM energy transmission by the antenna element due for example to energy being reflected back from the cavity to the EM probe and/or capacitive effects of the cavity, especially where the cavity has a low profile and is relatively close to the antenna. This might introduce dispersion and destructive/constructive EM radiation wave of the overall element. In some uses, reflections from the medium to which transmission is intended (e.g. a human or animal body) may also occur, potentially causing dispersion and destructive/constructive EM radiation wave of the overall element. Absorbers covering the cavity from inside (e.g. absorbing layer 215) and/or absorbers on conducting parts of the antenna (210) element may suppress such effect for example by suppressing ringing between for example spiral arms and cavity and/or spiral arms and medium to which transmission is intended, and improve flatness and polarization of EM energy that is transmitted in the desired direction.

In embodiments where the EM radiation absorbing layer is used, the attachment and/or placing in proximity of the EM probe with the EM radiation absorbing layer to a dielectric medium such as a skin of a human or animal body may encounter above described effects. For example, the properties of skin are such that putting an antenna in touching proximity to it may create absorbing effects. Thus, by placing an antenna with an EM radiation absorbing layer, such as for example the one described in FIG. 3A, in proximity to a skin, the behavior of the antenna might change due to absorbing effect that may be created in a non-covered area (or area that is not covered with EM radiation absorbing layer) of the antenna, for example in an area having a radius of Ra or less. This absorbing effect may in turn cause a decline in the effectiveness of the antenna in the higher frequency band, reducing the effective band that is usable for the antenna. In addition, since the properties of skin are not constant and may change to various physiological changes (for example sweating), and since the mechanical coupling of the EM probe to the skin may also change, due for example to movements, the behavior of the EM probe may be affected in an inconstant manner which may be less desirable.

EXAMPLES

Reference is now made to the following examples, which together with the above descriptions; illustrate some embodiments of the invention in a non-limiting fashion.

Figure 6:
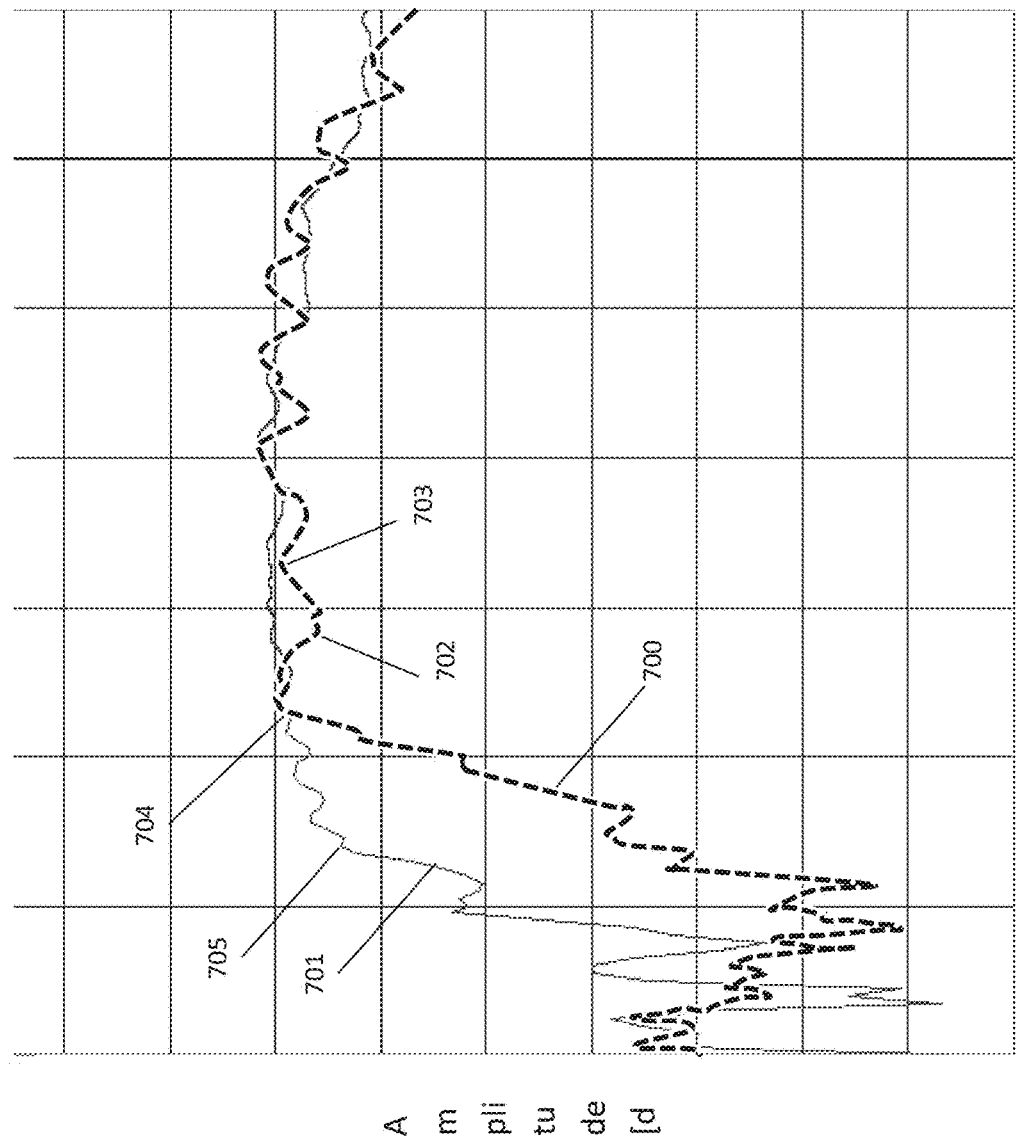
FIG. 6 is a graph depicting an amplitude response of a system which comprises two EM probes, each having a planar spiral antenna wherein one of the EM probes transmits to the other, via a human thorax, from back to chest, or from chest to back, according to some embodiments of the present invention.

Reference is now made to FIG. 6 which is a graph depicting the amplitude response of a system which comprises two spiral EM probes, each having a spiral antenna wherein one of the EM probes transmits to the other, via a human thorax, from back to chest, or from chest to back. The dashed line 700 represents measurements taken in a system where the EM probes do not comprise an EM radiation absorption layer (see for example the antenna of FIG. 2C) and the continuous line 701 represents a system where the EM probes are as depicted and described in relation to FIG. 3A (without optional ring shape 204). The Y axis denotes amplitude and X axis denotes a linear range of frequencies. Both axes are relative since the amplitude behavior depends on the medium through which the EM energy propagated and the design can be implemented in various physical dimension scales and thus the frequency response depends on the scale.

As depicted by dashed line 700, the antennas without an EM radiation absorption layer have a cutoff frequency at about point 704, as the amplitude declines significantly from that point and towards lower frequencies. As depicted by the continuous line 701 the EM probes with the EM radiation absorption layer exhibit lower cutoff frequency 705 relative to the EM probes without the EM radiation absorption layer (dashed line 700). In particular, the cutoff frequency exhibited for the continuous line is around 20% lower than the cutoff frequency exhibited for the dashed line, making the antennas with the EM radiation absorption layer more useable than the EM radiation absorption free antennas also for frequencies corresponding to the region between points 701 and 705.

As depicted in FIG. 6, when the EM probes include an EM radiation absorption layer (continuous line 701) the trend of amplitude change in response to frequency change is relatively linear or smooth in relation to the respective trend when the EM probes do not include the EM radiation absorption layer (dashed line 700). The linear trend is exhibited by a smoother line that has fewer notches and ripples (702 and 703). In some embodiments part of the EM energy, for example the lower frequency content, propagates on the spiral antenna from the feeding port is not radiated and reaches the end of the propagation path along the antenna. At a discontinuity present at the end of the propagation path a reflection is created resulting in non-monotonic spectral amplitude and phase response (i.e. notches) due to constructive and destructive interference between the advancing and reflected waves. Looking at FIG. 6, multiple notches can be seen in the dashed line for example such as 702, 703 whereas the continuous line exhibits a more monotonic and linear amplitude versus frequency behavior.

In some embodiments, where a circular polarization antenna is used, for example as depicted in FIG. 3A-3C the reflection created at the end of the propagation path may cause radiation polarization to become more elliptical or linear instead of circular in parts of the frequency band. An EM probe with an EM radiation absorbing layer reducing the abovementioned reflection related interference may maintain the circular polarization such that the horizontal and vertical components of the EM radiation are no more than 5 dB different at any given frequency.

It is expected that during the life of a patent maturing from this application many relevant systems and methods will be developed and the scope of the term a spiral antenna, an EM radiation absorption material, and an attachment unit is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An electromagnetic (EM) probe for monitoring at least one biological tissue, comprising:
    a spiral antenna having at least one spiral arm with a spiral path originated from a feeding point; and
    an EM radiation absorbing layer mounted along a plurality of turnings of said at least one spiral arm of the antenna, said EM radiation absorbing layer having:
    absorbing material between a plurality of gaps wherein the absorbing material is not present; and
    wherein said EM radiation absorbing layer is formed such that a spiral propagation path of said at least one spiral arm passes via said plurality of gaps;
    wherein the EM radiation absorbing layer is disposed in a plurality of concentric regions corresponding to portions of said spiral antenna having equal surface of antenna conductor;
    wherein any of said plurality of concentric regions has an EM radiation absorption coefficient greater than any other of said plurality of concentric regions it encloses;
    wherein an amount of the absorbing material disposed in each of said plurality of concentric regions gradually increases as a function of a distance of each of said plurality of concentric regions from said feeding point.

2. The EM probe of claim 1, wherein the spiral antenna is a wideband antenna.

3. The EM probe of claim 1, wherein the EM radiation absorbing layer is mounted in a common plane with a conductive element of the antenna.

4. The EM probe of claim 1, wherein the EM radiation absorbing layer is positioned to suppress EM currents.

5. The EM probe of claim 1, wherein said plurality of concentric regions frame a shape having no EM radiation absorbing layer.

6. The EM probe of claim 1, wherein at least one of density and concentration of the absorbing material in said plurality of concentric regions decreases from an outer periphery of said EM radiation absorbing layer to a central point of said EM radiation absorbing layer.

7. The EM probe of claim 6, wherein said central point coincides with a boresight of said antenna.

8. The EM probe of claim 6, wherein said central point coincides with said feeding point of said antenna.

9. The EM probe of claim 6, wherein said central point coincides with a geometric center of said antenna.

10. The EM probe of claim 1, wherein the EM radiation absorbing layer is parallel to a surface of the EM antenna.

11. The EM probe of claim 1, wherein said plurality of concentric regions have a geometric center that coincides with a boresight of said spiral antenna.

12. A method of producing an electromagnetic (EM) probe for monitoring at least one biological tissue, comprising:
   providing a spiral antenna having a feeding point and at least one conductive arm; and
   applying a layer of an EM absorbing material over a plurality of turnings of said spiral arm of said antenna, the layer is applied in a plurality of concentric regions corresponding to portions of said spiral antenna having equal surface area of the at least one conductive arm, each of said plurality of concentric regions having EM radiation absorption coefficient greater than any other of said concentric regions it encloses;
   said layer having:
   absorbing material between a plurality of gaps wherein the absorbing material is not present;
   wherein the plurality of concentric regions are formed such that a spiral propagation path of said spiral arm passes via the plurality of gaps;
   wherein the amount of the absorbing material in each of said plurality of concentric regions gradually increases as a function of a distance of each of said concentric regions from said feeding point.

13. An array configuration comprising a plurality of EM probes for monitoring at least one biological tissue, wherein each of the plurality of EM probes comprises
   a spiral antenna having at least one spiral arm with a spiral path originated from a feeding point; and
   an EM radiation absorbing layer mounted along a plurality of turnings of said at least one spiral arm of the antenna, said EM radiation absorbing layer having:
   absorbing material between a plurality of gaps wherein the absorbing material is not present; and
   wherein said EM radiation absorbing layer is formed such that a spiral propagation path of said at least one spiral arm passes via said plurality of gaps;
   wherein the EM radiation absorbing layer is disposed in a plurality of concentric regions corresponding to portions of said spiral antenna having equal surface of antenna conductor;
   wherein any of said plurality of concentric regions has an EM radiation absorption coefficient greater than any other of said plurality of concentric regions it encloses;
   wherein an amount of the absorbing material disposed in each of said plurality of concentric regions gradually increases as a function of a distance of each of said plurality of concentric regions from said feeding point.

14. The array configuration of claim 13, wherein the spiral antenna is a wideband antenna.

15. The array configuration of claim 13, wherein the EM radiation absorbing layer is mounted in a common plane with a conductive element of the antenna.

16. The array configuration of claim 13, wherein the EM radiation absorbing layer is positioned to suppress EM currents.

17. The array configuration of claim 13, wherein said plurality of concentric regions frame a shape having no EM radiation absorbing layer.

18. The array configuration of claim 13, wherein at least one of density and concentration of the absorbing material in said plurality of concentric regions decreases from an outer periphery of said EM radiation absorbing layer to a central point of said EM radiation absorbing layer.

* * * * *